Figure 1:
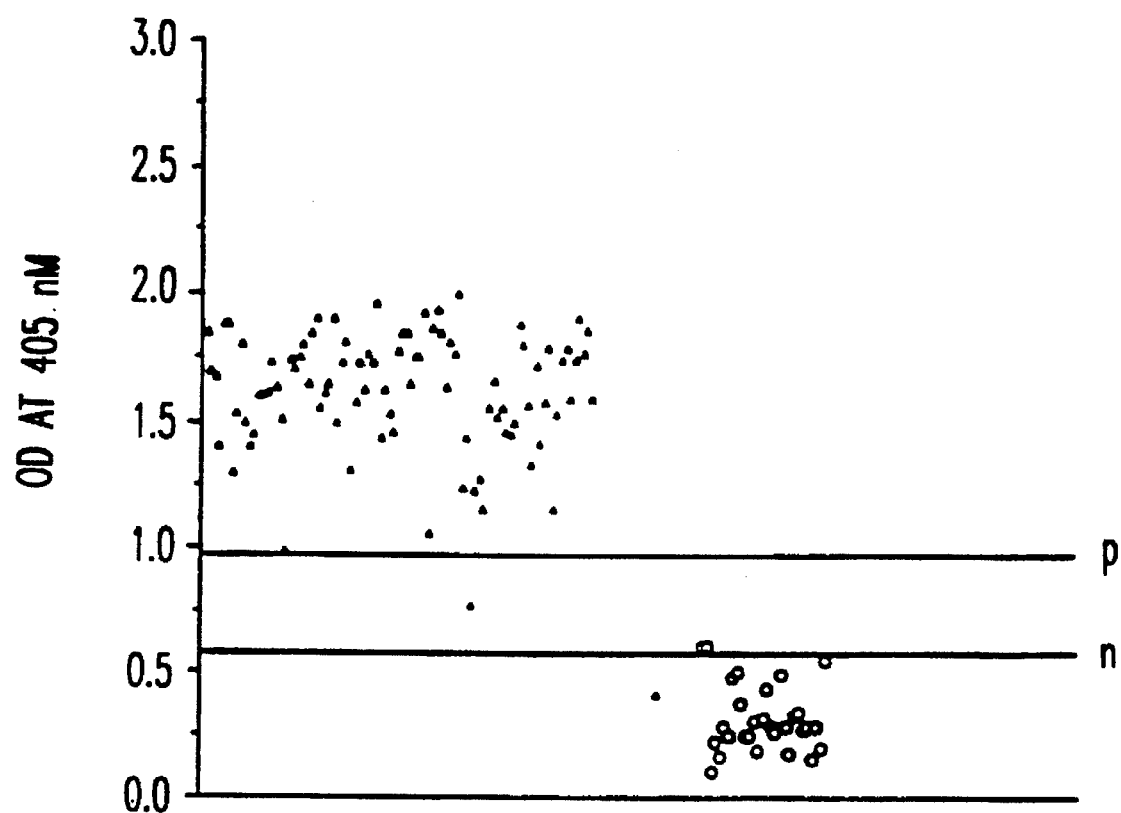

United States Patent [19]

Avrameas et al.

[11] Patent Number: 5,648,209
[45] Date of Patent: Jul. 15, 1997

[54] SPECIFIC PEPTIDE FRAGMENT OF THE FELINE IMMUNODEFICIENCY VIRUS (FIV), AND ITS USE AS A DIAGNOSTIC REAGENT

[75] Inventors: Alexandre Avrameas, Vitry-Sur-Seine; Gianfranco Pancino, Paris; Pierre Sibille, La Varenne; Pierre Sonigo; Arthur Donny Strosberg, both of Paris, all of France

[73] Assignee: Centre National de la Recherche Scientifique-CNRS, Paris Cedex, France

[21] Appl. No.: 487,485

[22] Filed: Jun. 7, 1995

[30] Foreign Application Priority Data

Jun. 9, 1994 [FR] France .................. 94 07062

[51] Int. Cl.⁶ ........................ C12Q 1/70
[52] U.S. Cl. ................ 435/5; 435/7.1; 435/7.9; 435/7.92; 435/7.94; 435/975; 436/518; 436/528; 436/531; 436/64; 436/804; 436/805; 530/326; 530/826
[58] Field of Search ............... 435/5, 7.1, 7.72, 435/7.9, 7.92, 7.93, 7.94, 7.95, 975; 436/518, 528, 531, 64, 804, 805; 530/324–328, 530, 826

[56] References Cited

FOREIGN PATENT DOCUMENTS

0557458A1  1/1994  European Pat. Off. .
WO92/22573  12/1992  WIPO .
WO93/01304  1/1993  WIPO .

OTHER PUBLICATIONS

Research In Virology, vol. 144, No. 3, Mai 1993, Paris, France, Pages 209–218. A. Avrameas, et al, "Serological Diagnosis of Feline Immunodeficiency Virus Infection Based on Synthetic Peptides from Env Glycoproteins".

*Primary Examiner*—Christine M. Nucker
*Assistant Examiner*—Jeffrey Stucker
*Attorney, Agent, or Firm*—Oblon, Spivak, McClelland, Maier & Neustadt, P.C.

[57] ABSTRACT

Specific peptide fragment from the feline immunodeficiency virus (FIV), and its use as a diagnostic reagent.

The said peptide fragment, derived from the Env protein of the Wo strain of the feline immunodeficiency virus (FIV) (peptide P253), corresponds to positions 693–709 of the said Env protein and exhibits the following sequence:

Leu-Gly-X-Asn-Gln-Asn-Gln-Phe-Phe-X-Lys-Val-Pro-Ser-Ala-, in which X represents a cysteine or a serine, as follows:

Leu-Gly-Cys-Asn-Gln-Asn-Gln-Phe-Phe-Cys-Lys-Val-Pro-Ser-Ala (SEQ ID NO: 1),

Leu-Gly-Ser-Asn-Gln-Asn-Gln-Phe-Phe-Ser-Lys-Val-Pro-Ser-Ala (SEQ ID NO: 2),

Leu-Gly-Cys-Asn-Gln-Asn-Gln-Phe-Phe-Ser-Lys-Val-Pro-Ser-Ala (SEQ ID NO: 3),

Leu-Gly-Ser-Asn-Gln-Asn-Gln-Phe-Phe-Cys-Lys-Val-Pro-Ser-Ala (SEQ ID NO: 4).

4 Claims, 1 Drawing Sheet

SPECIFIC PEPTIDE FRAGMENT OF THE FELINE IMMUNODEFICIENCY VIRUS (FIV), AND ITS USE AS A DIAGNOSTIC REAGENT

The present invention relates to a specific peptide fragment of the feline immunodeficiency virus (FIV), and to its use as a diagnostic reagent.

Feline immunodeficiency is due to a lentivirus, feline immunodeficiency virus (FIV), which exhibits a genetic structure which is similar to that of the lentiviruses of primates (HIV and SIV).

Feline immunodeficiency poses a considerable problem for veterinary health in as much as a substantial number of cats infected with FIV have been detected in the United States, in Japan and in Europe (5 to 30% of animals).

Several independent viral isolates have been prepared across the world, and a certain number of studies have been carried out in order to demonstrate the structure of the isolated strains, in particular as regards the American strain Petaluma [R. L. TALBOTT et al. (Natl. Acad. Sci. USA, 1989, 86, 5743–5747; T. R. PHILIPPS et al. (J. Virol., 1990, 64, 10, 4605–4613)], the Japanese strains (the TM1 and TM2 strains) [T. MIYAZAWA et al. (Arch. Virol., 1989, 108, 59–68)] or the Swiss isolates (FIVZ1 and FIVZ2) [S. MORIKAWA et al., (Virus Research, 1991, 21, 53–63)].

The nucleotide sequences of three proviral clones derived from American FIV isolates (Petaluma strain) have been described (clones FIV34TF10, FIV14 and isolate PPR) [R. A. OLMSTED et al., (Proc. Natl. Acad. Sci. USA, 1989, 86, 2448–2452); T. R. PHILIPPS et al., 1990; R.L. TALBOTT et al., (Proc. Natl. Acad. Sci. USA, 1989, 86, 5743–5747)] and compared with two Swiss isolates (S. MORIKAWA et al.). This comparison led S. MORIKAWA et al. to specify the presence of certain conserved regions and certain variable regions within the env gene of FIV.

French strains have also been isolated (strains Wo and Me) [MORAILLON A. et al., 1992, Vet. Mic., 31, 41–45, *In vitro properties and experimental pathogenic effect of three feline immunodeficiency viruses isolated from cats with terminal diseases*].

These different results have made it possible to develop a certain number of tests for detecting seropositive animals; those which may particularly be cited are:

ELISA tests which use recombinant p24 or p17 Gag proteins (Reid G. et al., 1991, AIDS, 5, 1477–1483); such tests have the disadvantage of giving rise to falsely negative reactions, since anti-Gag antibodies are not consistently present (FURUYA et al., 1992, Arch. Virol., 124, 355–361), ELISA tests which use a complete virus lysate, which is bound to a solid support and obtained from fibroblasts which are infected with FIV (O'Connor et al. J. Clin. Microbiol, 1989, 474–479; Steinman et al., J. Gen. Virol., 1990, 71, 701–706); such tests have the disadvantage of giving rise, at one and the same time, to falsely negative reactions and to falsely positive reactions, ELISA tests which use a synthetic peptide which is conjugated to peroxidase (Synbiotics); such tests also have the disadvantage of giving rise, at one and the same time, to falsely negative reactions and falsely positive reactions, ELISA tests which use synthetic peptides which are derived from the Env protein, such as described in Application EP 0 577 458, which correspond to ± conserved epitopes of the said Env protein, such as:

a fragment which includes a segment of 37 amino acids, designated SU1, which corresponds to positions 253–289 of the Env sequence (Wo strain);

a fragment which includes a segment of 37 amino acids, designated SU2, which corresponds to positions 388–424 of the Env sequence, which segment contains at least one epitope which includes the sequence: $\text{Trp}^{398}$-Glu-Trp-Arg-Pro-Asp-Phe-Glu-Ser-Glu-$\text{Lys}^{408}$ (peptide designated P240);

a fragment which includes a segment of 26 amino acids, designated SU3, which corresponds to positions 467–492 of the Env protein sequence of FIV Wo;

a fragment which includes a segment of 21 amino acids, designated SU4, which corresponds to positions 508–528 of the Env protein sequence of FIV Wo;

a fragment which includes a segment of 35 amino acids, designated SU5, which corresponds to positions 572–606 of the Env protein sequence of FIV Wo;

a fragment which includes a segment of 51 amino acids, designated TM1, which corresponds to positions 595–647 of the Env protein sequence of FIV Wo;

a fragment which includes a segment of 31 amino acids, designated TM2, which corresponds to positions 681–711 of the Env protein sequence of FIV Wo, which segment contains an epitope which includes the sequence: $\text{Gln}^{699}$-Asn-Gln-Phe-Phe-Cys-$\text{Lys}^{705}$ or the sequence $\text{Cys}^{697}$-Asn-Gln-Asn-Gln-Phe-Phe-Cys-$\text{Lys}^{705}$ (peptide designated P237);

a fragment which includes a segment of 45 amino acids, designated TM3, which corresponds to positions 744–788 of the Env protein sequence of FIV Wo, which segment contains an epitope which includes the sequence: $\text{Gln}^{764}$-Leu-Gln-Glu-Trp-Glu-Asp-Trp-Val-Gly-Trp-Ile-Gly-Asn-$\text{Ile}^{778}$ or the sequence $\text{Gln}^{763}$-Gln-Leu-Gln-Glu-Trp-Glu-$\text{Asp}^{770}$ (peptide designated P241) or the sequence $\text{Val}^{772}$-Gly-Trp-Ile-Gly-Asn-Ile-$\text{Pro}^{779}$ (peptide designated P242);

a fragment which includes a segment of 29 amino acids, designated TM4, which corresponds to positions 826–854 of the Env protein sequence of FIV Wo.

Certain of these SU and TM peptides, which are described in Application EP 0 577 458, are considered as being universal fragments (in particular those included in SU2, TM2 and TM3), that is to say fragments recognizing the antibodies produced by an FIV, if it is present, whatever the strain, while others are considered to be fragments which are specific for the Wo strain (in particular SU3 and TM4).

Although this latter test exhibits a sensitivity which is clearly improved in comparison with the other, aforementioned tests, the Applicant has found that the sensitivity and the specificity of ELISA tests which are carried out using synthetic peptides can be further improved so as effectively to achieve a reliability of the order of 100%, so as to have available a test which is particularly suitable for routine veterinary tests.

The present invention relates to a peptide fragment which is derived from the Env protein of FIV Wo and which corresponds to positions 693–709 of the said Env protein.

The said peptide exhibits the following sequence Leu-Gly-X-Asn-Gln-Asn-Gln-Phe-Phe-X-Lys-Val-Pro-Ser-Ala-, in which X represents a cysteine or a serine, as follows:

Leu-Gly-Cys-Asn-Gln-Asn-Gln-Phe-Phe-Cys-Lys-Val-Pro-Ser-Ala (SEQ ID NO: 1),

Leu-Gly-Ser-Asn-Gln-Asn-Gln-Phe-Phe-Ser-Lys-Val-Pro-Ser-Ala (SEQ ID NO: 2),

Leu-Gly-Cys-Asn-Gln-Asn-Gln-Phe-Phe-Ser-Lys-Val-Pro-Ser-Ala (SEQ ID NO: 3),

Leu-Gly-Ser-Asn-Gln-Asn-Gln-Phe-Phe-Cys-Lys-Val-Pro-Ser-Ala (SEQ ID NO: 4)

Unexpectedly, selecting a peptide which was longer than the previously described peptide P237 for diagnosing FIV infections did not lead to any falsely positive results or falsely negative results being detected.

The difference in reactivity between peptide P237 (9 residues) and peptide P253 (15 residues) can be due to the fact that these two peptides fold differently; in particular, the peptide according to the present invention (P253) is better able to imitate the conformation of the corresponding domain of the envelope glycoprotein, or else can be more effectively exposed following binding to a solid support; the antibodies which are able to react with peptide P253 would be more frequently encountered in infected feline sera, and the 5 amino acids which are situated at the C-terminal end of peptide P253 appear to be essential for recognizing all the sera of infected cats.

The present invention also relates to a method for screening for an FIV infection, characterized in that it consists in detecting the anti-FIV antibodies which may be present in a biological sample with the aid of the P253 peptide according to the invention, which peptide is fixed, where appropriate, to a suitable solid support, by bringing the said biological sample into contact with the said peptide, to which the anti-FIV antibodies bind, if such antibodies are present in the sample to be analysed, with the result being read by a suitable means, in particular EIA, RIA or fluorescence.

This method renders it possible, in particular, to verify the seroconversion of vaccinated animals or to carry out serological investigations for epidemiological purposes.

Unexpectedly, the said method renders it possible to establish the presence of an FIV infection whatever the strain might be (universal reagent, as specified above).

Equally unexpectedly, when the said P253 peptide is employed in a test for detecting an FIV infection, it appears to be more sensitive for detecting positive sera than is the P237 peptide.

The present invention furthermore relates to a kit, which is ready for use, for implementing the method for screening for an FIV infection, characterized in that it comprises, in addition to useful quantities of suitable buffers for implementing the said detection, appropriate doses of the P253 peptide according to the invention.

In addition to the preceding provisions, the invention also includes further provisions which will emerge from the description which follows, which refers to exemplary embodiments of the method to which the present invention relates.

It should be understood, however, that these examples are given solely by way of illustrating the subject matter of the invention of which they in no way constitute a limitation.

EXAMPLE 1

Comparison of the P237 (Application EP No. 577 458) and P253 (according to the invention) peptides in an ELISA test 1) Protocol 50 μl of a 5 μg/ml solution of peptides in 0.1M sodium carbonate, pH 9.6, is adsorbed onto the wells of a microtitration plate (Dynatech Immulon® 2), at 4° C. for one night.

The wells are then washed 5 times with PBS. The residual adsorption sites of the microplates are saturated at 37° C. by incubating with 250 μl of 3% bovine serum albumin in PBS for 3–4 hours.

After 5 washes with PBS containing a 0.1% Tween® washing buffer (WB buffer), 50 μl of cat serum, diluted 1/10 in a PBS buffer containing BSA (1%) and Tween® 20 (0.1%), are incubated in the wells at room temperature for 1 hour.

After washing 3 times with the WB buffer, anti-cat immunoglobulins which are conjugated to peroxidase (0.5 μg/ml) (Kirkegaard and Perry Laboratories Inc), are added at room temperature for one hour.

After 5 washes with PBS, the conjugate bound to peroxidase is visualized using 0.5 mg/ml 2,2'-azino-bis(3-ethylbenzthiazoline-6-sulphonic acid) (ABTS, Sigma) in a phosphate-citrate buffer, pH 5.3, which contains 0.03% sodium perborate (Aldrich).

2) Results

The assays are carried out in duplicate. In order to be able to distinguish positive reactions, a limit value is calculated as follows:

$p = 3 \times m_{NC}$ (3 times the mean absorbance of negative control sera ($_{NC}$)).

The absorbance values (or OD for optical density) which are greater than p are regarded as indicating the presence of anti-FIV antibodies.

The absorbance values which are less than $n = 2 \times m_{NC}$ are regarded as indicating the absence of anti-FIV antibodies.

Table I below illustrates the results which were obtained with 184 cat sera, including 146 cat sera resulting from veterinary consultations, 18 sera from cats which were infected experimentally and 20 sera from healthy cats (SPF cats).

TABLE I

| P237 | P253 (SEQ ID N° 1) | Number of sera (%) |
|---|---|---|
| + | + | 110 (59.78) |
| − | + | 7 (3.80) |
| − | − | 67 (36.42) |
| | TOTAL | 184 (100) |

This table demonstrates that the P253 peptide is significantly more sensitive for detecting positive sera than is the P237 peptide.

EXAMPLE 2

Evaluation of the sensitivity and specificity of the P253 ELISA test

In order to assess and evaluate the sensitivity and the specificity of the P253 peptide (SEQ ID N° 1), the two peptides, P237 and P253, were compared in an ELISA, using the same sera as above, so as to determine which of the peptides gives the best specificity and the best sensitivity in comparison with a test carried out using complete virus lysate (Petchek test, IDEXX), (complete virus test), and with a GN sandwich ELISA test, which is regarded as a reference test and which corresponds to an ELISA test using a lectin which is derived from the plant *Galanthus nivalis* and which specifically recognizes the terminal D-mannose groups of the Env glycoprotein (GN test).

The results are illustrated in Table II below:

TABLE II

| P237 Test | P253 Test (SEQ ID N° 1) | Virus Lysate Test | GN ELISA Test | Number of Sera (%) |
|---|---|---|---|---|
| + | + | + | + | 102 (55.43) |
| + | + | − | + | 8 (4.35) |
| − | + | + | + | 7 (3.80) |
| − | − | + | + | 1 (0.54) |
| − | − | + | − | 11 (5.98) |
| − | − | − | − | 55 (29.9) |
| | | | Total | 184 (100) |

It emerges from Table II that:

in 157 cases (85.33%), the two peptides give the same results as the test based on complete virus; however, the P253 test is significantly more sensitive than the P237 test, which produces falsely negative results (7 sera);

no falsely positive result is observed, something which is of major importance in the context of routine veterinary tests, while the complete virus test shows 11 falsely positive sera as well as 8 falsely negative sera:

the 11 sera which give positive results with the complete virus test (false positives) and negative results with the P253 ELISA test were obtained from cats which were not exhibiting any symptom which was particularly suggestive of an FIV infection, apart from a number of cases of gingivitis;

when interpreted in the light of clinical findings, the P253 test also suggests that the 8 sera which were negative in the complete virus test correspond to falsely negative results insofar as 6 of the 8 sera which were negative in the complete virus test and positive in the P253 ELISA test were obtained from sick cats which exhibited fever, diarrhoea, gingivitis and other symptoms suggestive of an FIV infection. The other two sera were obtained from cats which exhibited nervous and behavioural disorders;

in one single case, the P253 peptide gives a result which diverges from that obtained with the GN test; this divergence in the results can be explained by mutations having taken place, in this particular instance, in the envelope sequence corresponding to the peptide, which sequence has otherwise been perfectly constant in all the FIV isolates sequenced to date. Alternatively, it may be supposed that the anti-P253 antibodies in this particular serum were complexed in the form of immune complexes.

FIG. 1 illustrates the results which were obtained by comparing the P253 test and the GN test; this FIG. 1 shows the optical densities which were obtained with the different sera tested with the P253 test, and their distribution (each point represents one serum) on either side of the p and n optical density values as defined above; the same sera were tested with the GN ELISA test: the ▲s represent the sera which were positive in the GN ELISA test while the ○s represent the sera which were negative in the GN ELISA test.

These results confirm:

that only one serum which is positive in the GN ELISA falls below the negative limit value $n=2 \times m_{NC}$ of the P253 test, and that 3 sera are located between the p and n limit values; FIG. 1 shows that 2 of these 3 sera are negative in the confirmatory GN ELISA test while the third is regarded as positive.

These data therefore correspond to those of Table II above.

The abovementioned GN test is carried out under the following conditions:

This GN test, based on the protocol described by GILL-JAM (*AIDS Res.* and *Hum. Retrovir.*, 1993, 9, 431–438), comprises, more precisely, the coating of microtitration plates (Dynatech Immulon® 2) with 1 μg of GN lectin (Sigma, L-8275) in 100 μl of 0.1M sodium carbonate buffer, pH 9.6, at room temperature for one night.

After 3 washes with PBS, the plates are incubated for 2 hours, at room temperature, with PBS containing 10% foetal calf serum.

The plates are then washed 3 times with the abovementioned WB buffer.

100 μl of supernatant from FL4 cells which are chronically infected with FIV ($10^6$ cells/ml), and containing 0.25% Empigene®-BB (Calbiochem.), are then added to each well, and the plates are incubated at 4° C. for one night.

After 3 washes with the WB buffer, the cat sera are incubated at room temperature for 2 hours (diluted 1:400 in a PBS, 0.1% Tween 20, 10% foetal calf serum buffer).

Reaction with an anti-cat immunoglobulin which is conjugated to peroxidase, and colour development in the presence of substrate, is carried out as described above for the ELISA test.

These results demonstrate the importance of reagent selection within the context of routine veterinary tests.

Table III highlights the sensitivity and specificity of the P253 test.

TABLE III

| | Number of sera (%) |
|---|---|
| true positive | 117 (63.6%) |
| true negative | 66 (35.8%) |
| false positive | 0 |
| false negative | 1 (0.54%) |
| sensitivity | 98.9% |
| specificity | 100% |

The P253 ELISA test demonstrates a specificity and a sensitivity which are significantly greater than those obtained with the complete virus lysate test; only 3 sera required confirmation with the GN ELISA test.

Furthermore, the P253 test displays an increase in specificity and sensitivity when it is compared with immunoblots and with RIPAs (radio-immmunoprecipitation assays), which often lead to non-specific cross-reactions.

EXAMPLE 3

Comparison of the P253 ELISA test with an ELISA test which uses another synthetic peptide This P253 ELISA test was also compared with another ELISA test which uses a synthetic peptide conjugated to peroxidase, which peptide corresponds to the immunodominant domain of the transmembrane region of the Env protein of FIV (FIV Viracheck\, SYNBIOTICS CORPORATION).

SPF negative control cats, experimentally infected cats and naturally infected cats were tested using this peptide.

Differences are observed:

a cat serum which is experimentally infected with the LE strain does not react with the peptide conjugated to peroxidase although it is positive in all the other tests. 2 sera from the naturally infected cats did not react with the said peptide conjugated to peroxidase although they were positive in the P237, P253 and GN tests.

These results demonstrate the importance of selecting the most appropriate reagent.

Contrary to the P253 and GN tests, the peptide conjugated to peroxidase also gives rise to falsely negative results.

Use of the P253 peptide, which encompasses 5 additional amino acid residues at the C-terminal end, makes it possible to increase the sensitivity of the test appreciably and to recognize practically all infected sera.

As emerges from the above, the invention is in no way limited to those of its embodiments and modes of application which have been described more explicitly; on the contrary, it encompasses all the variants which the person skilled in the art can bring to mind without diverging from the scope and range of the present invention.

We claim:

1. A peptide derived from feline immunodeficiency virus strain Wo (FIV$_{Wo}$) envelope protein, amino acids 693–703, said peptide having the sequence Leu-Gly-Cys-Asn-Gln-Asn-Gln-Phe-Phe-Cys-Lys-Val-Pro-Ser-Ala (SEQ ID NO:1).

2. A method of screening for FIV infection comprising
a) attaching the peptide of claim 1 to a solid support,
b) contacting a biological sample with the peptide to allow binding of anti-FIV antibodies to the peptide for a time sufficient to form a peptide-antibody complex,
c) reacting said complex with anti-feline antibodies,
d) detecting the anti-feline antibodies if present.

3. The method of claim 2 wherein the anti-feline antibodies have a label selected from the group consisting of a radioisotope, an enzyme, and a fluorophore.

4. A kit for the diagnosis of FIV infection comprising the peptide of claim 1 and suitable buffers, labels, and control sera.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:1:

```
Leu Gly Cys Asn Gln Asn Gln Phe Phe Cys Lys Val Pro Ser Ala
 1               5                  10                  15
```

( 2 ) INFORMATION FOR SEQ ID NO:2:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:2:

```
Leu Gly Ser Asn Gln Asn Gln Phe Phe Ser Lys Val Pro Ser Ala
 1               5                  10                  15
```

( 2 ) INFORMATION FOR SEQ ID NO:3:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:3:

```
Leu Gly Cys Asn Gln Asn Gln Phe Phe Ser Lys Val Pro Ser Ala
 1               5                  10                  15
```

( 2 ) INFORMATION FOR SEQ ID NO:4:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:4:

```
Leu Gly Ser Asn Gln Asn Gln Phe Phe Cys Lys Val Pro Ser Ala
 1               5                  10                  15
```